United States Patent

Schneider et al.

[11] 4,087,270
[45] May 2, 1978

[54] HERBICIDAL-N-(3-AMINO-2,4-DINITRO-6-TRIFLUOROMETHYLPHENYL)-PYRROLIDONES

[75] Inventors: Louis Schneider, Elizabeth; David E. Graham, Westfield, both of N.J.

[73] Assignee: GAF Corporation, New York, N.Y.

[21] Appl. No.: 773,817

[22] Filed: Mar. 3, 1977

[51] Int. Cl.$^2$ .................. C07D 207/24; C07D 207/26; A01N 9/22
[52] U.S. Cl. .............................. 71/95; 260/326.5 FL; 260/326.82
[58] Field of Search ................ 260/326.5 FL, 326.82; 71/95

[56] References Cited

U.S. PATENT DOCUMENTS 3,586,725  6/1971  Hunter ................................ 260/646

Primary Examiner—Jose Tovar
Attorney, Agent, or Firm—Walter C. Kehm; Walter Katz

[57] ABSTRACT

The present invention provides herbicidal-N-(3-amino 2,4-dinitro-6-trifluoromethylphenyl)-pyrrolidones having the formula:

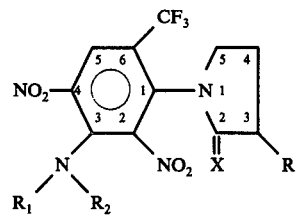

where
X is oxygen or sulfur, and R, $R_1$ and $R_2$ are selected from among H or lower alkyl, of up to 4 carbon atoms.

The compounds of this invention are prepared by reacting a 2,4-dihalo-3,5-dinitrobenzotrifluoride with an amine, followed by condensation of the amino intermediate with the alkali metal salt of a pyrrolidone.

The N-(substituted-phenyl)-pyrrolidones described herein show good herbicidal activity, particularly pre-emergence activity against Japanese millet and crabgrass.

14 Claims, No Drawings

HERBICIDAL-N-(3-AMINO-2,4-DINITRO-6-TRI-FLUOROMETHYLPHENYL)-PYRROLIDONES

BACKGROUND OF THE DISCLOSURE

1. Field of the Invention

This invention relates to herbicidal compounds which are N-(substituted-phenyl)-pyrrolidones.

2. Description of the Prior Art

Aromatic compounds are known in the art as being useful agricultural chemicals. Accordingly, it is the object of this invention to provide new and useful compounds which exhibit good herbicidal activity.

SUMMARY OF THE INVENTION

The present invention provides herbicidal-N-(3-amino-2,4-dinitro-6-trifluoromethylphenyl)-pyrrolidones having the formula:

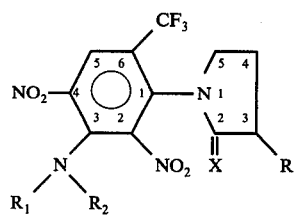

where

X is oxygen or sulfur, and R, $R_1$ and $R_2$ are selected from among H or lower alkyl, of up to 4 carbon atoms.

The compounds of this invention are prepared by reacting a 2,4-dihalo-3,5-dinitrobenzotrifluoride with an amine, followed by condensation of the amino intermediate with the alkali metal salt of a pyrrolidone.

The N-(substituted-phenyl)-pyrrolidones described herein shows good herbicidal activity particularly pre-emergence activity against Japanese millet and crabgrass.

DESCRIPTION OF THE PREFERRED EMBODIMENTS

The compounds (III) of this invention are prepared by condensing a 4-amino-2-halo-3,5-dinitrobenzotrifluoride (I) with an alkali metal salt of a pyrrolidone (II), as follows:

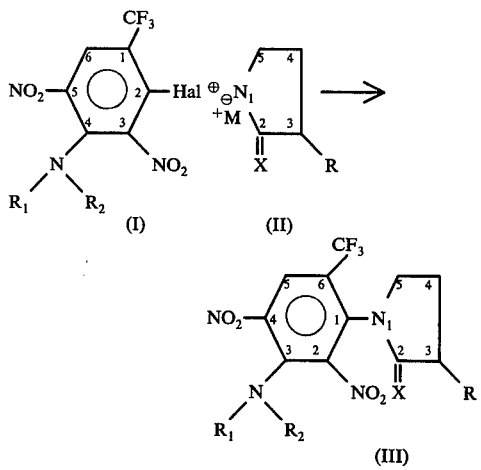

where Hal is a halogen, $M^+$ is an alkali metal salt, and R, $R_1$ and $R_2$ are as previously defined.

I is produced by a two-step process. The first step involves dinitration of the corresponding halobenzotrifluoride compound in a mixture of nitric and sulfuric acids as described in U.S. Pat. No. 3,586,725. In the second step, the halodinitrobenzotrifluoride intermediate is aminated to produce I, which is also described in said patent. II is prepared by reacting pyrrolidone with an alkali methoxide.

The condensation reaction is carried out by stirring the reactants for an extended period of time at room temperature, in a suitable solvent, and then at an elevated temperature for an additional period of time. Upon completion of the reaction, the solvent is removed and the desired product is separated by partition extraction. The extraction agent then is removed by rotoevaporation and the product is crystallized from a suitable solvent.

The compounds of this invention are especially useful as agricultural herbicides. Usually they are applied to the soil at the rate of about 1 to 25 lbs. per acre or as a foliar spray at concentrations of about 31 to 260 ppm. They show particularly effective herbicidal activity against Japanese millet and crabgrass.

The materials of the present invention may be applied to the soil or sprayed on the weeds on site at a rate of about 1 or less to about 25 pounds per acre depending on various circumstances of the susceptibility of the weed to the herbicide, the weather, the stage of growth and various other factors. The material may be applied as a dust or spray. As a dust it is more practical to extend it with diluents such as bentonite, chalk, clay, diatomaceous earth, fullers earth, mica, ground slate or any of the other usual carriers for agricultural chemicals. As a spray it may be incorporated into water as a solution. The higher molecular weight compounds may be dissolved first in a solvent, such as an alcohol, or a petroleum fraction, such as isoparaffinic hydrocarbons, naphtha or kerosene, which may be dissolved in a suitable solvent and fogged or sprayed without water. Usually it is desirable to incorporate emulsifying agents and other wetting agents to insure complete contact with the weed.

The following are examples of preparation of representative compounds of the invention, and are presented by way of illustration, and are not intended to be limiting unless otherwise specified.

EXAMPLE 1

N-(3-Diethylamino-2,4Dinitro-6-Trifluoromethylphenyl)-Pyrrolidone

Benzene (250 cc) was charged into a 500 cc 4-neck flask equipped with a stirrer, reflux condenser, drying tube, thermometer and dropping funnel. A 25 cc portion of benzene was removed by distillation. The benzene was cooled to 30° and 10.4 g sodium methoxide (0.18 m) was added. The mixture was heated to reflux (72°) and 17.0 g 2-pyrrolidone (0.2 m) were added in 0.25 hr. at 72°–78°. A total of 140 cc of benzene-methanol was removed by azeotropic distillation. Dimethylformamide (50 cc) was added and the distillation continued. A mixture of DMF-benzene (48 cc) was then removed by a second azeotropic distillation.

The residue, which contained sodium pyrrolidone, was cooled to 40°, and a solution of 34.2 g of 2-chloro-4-diethylamino-3,5-dinitrobenzotrifluoride (0.1 m) in 50 cc of DMF was added in 0.5 hr. at 40°-46°. The reaction mixture was heated at 112°-115° for 21.5 hr., cooled, and partitioned between 100 cc of tolune and 200 cc of water. The toluene phase was given 5 × 100 cc water washes, and the toluene was removed by rotary evaporation, leaving 21.0 g of residue. The residue then was vacuum distilled using a micro short-path distillation apparatus. The product (5.5 g) distilled at 170°-180° (0.1-0.2 mm). The yellow distillate was recrystallized twice from 1 part of methanol to yield 2.2 g, 5.0% yield; mp 94°-95°; IR(KBr) 3080 (CH aromatic), 2990 (CH aliphatic), 1710 (C=O), 1530 and 1340 cm$^{-1}$ (NO$_2$); NMR (CDCl$_3$) δ 8.1 (1, s, CH aromatic), 3.6 (2, t, CH$_2$NCO), 3.1 (4, q NCH$_2$-CH$_3$), 2.6-2.1 (4, m, CH$_2$CH$_2$C=O), 1.1 (6, t, CH$_3$).

Anal. Calcd for C$_{15}$H$_{17}$F$_3$N$_4$O$_5$: N, 14.36. Found: N, 14.52.

EXAMPLE 2

N-(3-Diethylamino-2,4-Dinitro-6-trifluoromethylphenyl)-Thiopyrrolidone

The procedure of Example 1 is followed except that thiopyrrolidinone (prepared as described in the liturature by reaction of pyrrolidone and phosphorous pentasulfide in refluxing benzene) is used in place of pyrrolidone, to provide the desired compound.

EXAMPLE 3

N-(3-Diethylamino-2,4-Dinitro-6-trifluoromethylphenyl)-3-Butylpyrrolidone

The procedure of Example 1 is followed except that 3-butylpyrrolidinone (prepared as described in the literature by reaction of pyrrolidone with butylene in isopropanol with di-t-butyl peroxide as a catalyst at 35° C for 16 hours) is used in place of pyrrolidone, to provide the desired product.

EXAMPLE 4

N-(3-Amino-2,4-Dinitro-6-Trifluoromethylphenyl)-Pyrrolidone

The procedure of Example 1 is followed except that 2-chloro-4-amino-3,5-dinitrobenzotrifluoride is used in place of the corresponding 4-diethylamino starting material to provide the desired product.

EXAMPLE 5

N-(3-Sec.-Butylamino-2,4-Dinitro-6-Trifluoromethylphenyl)-Pyrrolidone

The procedure of Example 1 is followed except that 2-chloro-4-sec.-butylamino-3,5-dinitrobenzotrifluoride is used in place of the corresponding 4-diethylamino starting material to provide the desired product.

EXAMPLE 6

Herbicidal Tests

Primary tests on the compound of Example 1 were made on two flats seeded with six species of representative monocotyledonous and dicotyledonous plants (Japanese millet and crabgrass). The test chemical was applied to one such flat immediately after it was seeded. The other flat contained plants on which the first true leaves had developed. Both of these flats were sprayed, simultaneously, with the test chemical at 2080 ppm, a rate sufficient to give 10 lb/acre (104 mg in 50 ml of water on 144 square inches). Diuron, 3-(3,4-dichlorophenyl)-1,1-dimethylurea as a standard was applied pre-emergence at the rate of 2.5, lb/acre. The response was rated 12 to 21 days after treatment on a scale of 0 to 10 where 0 represents no injury and 10 represents complete kill.

| Test Plant | Example 1 | Pre-Emergence Herbicidal Rati Standard (Diuron) |
|---|---|---|
| Japanese Millet | 8 | 10 |
| Crabgrass | 7 | 9 |

While the invention has been described with particular reference to certain embodiments thereof, it will be understood that certain modifications and changes may be made which are within the skill of the art. Therefore it is intended to be bound only by the appended claims.

What is claimed is:

1. N-(3-amino-2,4-dinitro-6-trifluoromethylphenyl)-pyrrolidones having the formula:

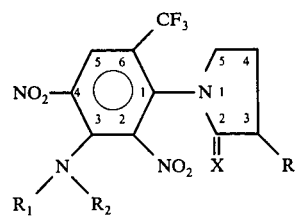

where
X is oxygen or sulfur, and R, R$_1$ and R$_2$ are selected from among H or lower alkyl, of up to 4 carbon atoms.

2. A compound according to claim 1 wherein X is oxygen.

3. A compound according to claim 1 wherein R is H.

4. A compound according to claim 1 wherein R$_1$ and R$_2$ are are H.

5. A compound according to claim 1 wherein R is lower alkyl.

6. A compound according to claim 1 wherein R$_1$ and R$_2$ are lower alkyl.

7. A compound according to claim 1 which is N-(3-diethylamino-2,4-dinitro-6-trifluoromethylphenyl)-pyrrolidone.

8. A compound according to claim 1 which is N-(3-diethylamino-2,4-dinitro-6-trifluoromethylphenyl)-thiopyrrolidone.

9. A compound according to claim 1 wherein R$_1$ is hydrogen and R$_2$ is lower alkyl.

10. A compound according to claim 1 which is N-(3-sec.-butylamino-2,4-dinitro-6-trifluoromethylphenyl)-pyrrolidone.

11. A compound according to claim 1 which is N-(3-diethylamino-2,4-dinitro-6-trifluoromethylphenyl)-3-butylpyrrolidone.

12. A compound according to claim 1 which is N-(3-amino2,4-dinitro-6-trifluoromethylphenyl)-pyrrolidone.

13. A method of controlling undesired weeds comprising applying thereto a herbicidally effective amount of a compound having the formula:

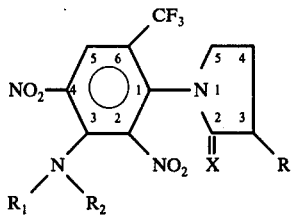

where

X is oxygen or sulfur, and R, $R_1$ and $R_2$ are selected from among H or lower alkyl, of up to 4 carbon atoms.

14. A herbicidal composition of matter comprising:

(a) a herbicidally effective amount of a 2,4-dihalo3,5-dinitrobenzotrifluoride having the formula:

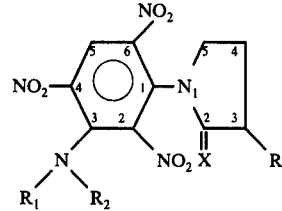

where

X is oxygen or sulfur, and R, $R_1$ and $R_2$ are selected from among H or lower alkyl, of up to 4 carbon atoms, and, (b) an inert carrier.

* * * * *